US012721848B2

(12) United States Patent
Lee et al.

(10) Patent No.: US 12,721,848 B2
(45) Date of Patent: Sep. 1, 2026

(54) PHARMACEUTICAL COMPOSITION FOR PREVENTING OR TREATING GRAFT VERSUS HOST DISEASE COMPRISING THIAMINE DERIVATIVES

(71) Applicant: Kyungpook National University Industry-Academic Cooperation Foundation, Daegu (KR)

(72) Inventors: In-Kyu Lee, Daegu (KR); Eun Jung Choi, Daegu (KR); Chang Hyun Jeon, Daegu (KR); Jae-Han Jeon, Daegu (KR)

(73) Assignee: Kyungpook National University Industry-Academic Cooperation Foundation, Buk-gu daegu (KR)

( * ) Notice: Subject to any disclaimer, the term of this patent is extended or adjusted under 35 U.S.C. 154(b) by 808 days.

(21) Appl. No.: 18/025,252

(22) PCT Filed: Sep. 15, 2021

(86) PCT No.: PCT/KR2021/012578
§ 371 (c)(1),
(2) Date: Mar. 8, 2023

(87) PCT Pub. No.: WO2022/060079
PCT Pub. Date: Mar. 24, 2022

(65) Prior Publication Data

US 2023/0310430 A1 Oct. 5, 2023

(30) Foreign Application Priority Data

Sep. 18, 2020 (KR) ........................ 10-2020-0120568

(51) Int. Cl.
*A61K 31/506* (2006.01)
*A23L 33/15* (2016.01)
*A61P 37/06* (2006.01)

(52) U.S. Cl.
CPC ............ *A61K 31/506* (2013.01); *A23L 33/15* (2016.08); *A61P 37/06* (2018.01)

(58) Field of Classification Search
CPC .... A61K 31/506; A61K 31/505; A61K 31/51; A61K 31/675; A23L 33/15; A23L 33/10; A61P 37/06; A23V 2200/324; A23V 2250/30; A23V 2002/00
See application file for complete search history.

(56) References Cited

U.S. PATENT DOCUMENTS

2017/0326163 A1 11/2017 Driscoll

FOREIGN PATENT DOCUMENTS

| | | | | |
|---|---|---|---|---|
| CN | 105147708 A | 12/2015 | | |
| KR | 10-2020-0016793 A | 2/2020 | | |
| KR | 10-2020-0050878 A | 5/2020 | | |
| WO | WO-2016015634 A1 * | 2/2016 | ................ | A61P 9/10 |

OTHER PUBLICATIONS

Saidu et al (Frontiers in Immunology, 2020; 11:578314 pp. 1-19) (Year: 2020).*

Extended European Search Report from corresponding European Patent Application No. 21869701.9, issued on Dec. 4, 2023.

Crane, S., et al, "The Attempted Enrichment of Beer with Thismine Alkyl Disulphides", Nutr Sci Vitaminol (Tokyo) Jun. 1983;29(3)381-7.

Spectrochimica acta. Part A, Molecular and biomolecular spectroscopy, Apr. 5, 2015, 140, 524-33, Abstract only.

Hamilton, B. K., "Current approaches to prevent and treat GVDH after allogenic stem cell transplantation", Hematology Am Soc Hematol Educ Program, Nov. 30, 2018;2018(1)228-235.

Steinberg, A., et al.; "Thiamine Deficiency in Stem Cell Transplant Patients: A Case Series With an Accompanying Review of the Literature", Clin Lymphoma Myeloma Leuk Sep. 14, 2014 SuppIS111-3.

Park, D., et al.; "Retrospective Analysis of Allogeneic Stem Cell Transplant Patients with Thiamine Deficiency", Biol Blood Marrow Transplant 24 (2018) S119-S290.

Oh, S.-H, "Detection of transketolase in bone marrow-derived insulin-producing cells: benfotiamine enhances insulin sythesis and glucose metabolis", Stem Cells and Development vol. 18, No. 1, 2009, pp. 7-46.

Lee, E-B., et al.; "The Preventative Effect of Fursulthiamine on Dietary Hypertension in Rats", Journal of Pharmacy, 1999, vol. 43, No. 1, pp. 91-97.

International Search Report from corresponding PCT Application No. PCT/KR2021/012578, dated Dec. 24, 2021.

* cited by examiner

*Primary Examiner* — Rayna Rodriguez
(74) *Attorney, Agent, or Firm* — Harness, Dickey & Pierce, P.L.C.

(57) ABSTRACT

The present invention relates to a pharmaceutical composition for preventing, treating, or ameliorating graft versus host disease (GVHD), comprising thiamine derivatives, in which the active ingredient of the pharmaceutical composition is fursultiamine, which can alleviate weight loss found in patients with GVHD, reduce the infiltration of liver and colon inflammatory cells, and effectively inhibit the production of allogeneic CD4+ IFNγ+ T cells, and thus can be effectively used for the prevention, treatment, or amelioration of GVHD.

8 Claims, 6 Drawing Sheets

PHARMACEUTICAL COMPOSITION FOR PREVENTING OR TREATING GRAFT VERSUS HOST DISEASE COMPRISING THIAMINE DERIVATIVES

CROSS-REFERENCE TO RELATED APPLICATIONS

This application is a national phase application of PCT Application No. PCT/KR2021/012578, filed on Sep. 15, 2021, which claims priority to Korean Patent Application No. 10-2020-0120568, filed on Sep. 18, 2020. The entire disclosures of the applications identified in this paragraph are incorporated herein by reference.

TECHNICAL FIELD

The present disclosure is made with the support of the Ministry of Science and ICT, Republic of Korea, under Project Identification No. 1711111722 and Project No. 2017R1A2B3006406, which was conducted in the research project named "New Therapeutic Mechanism of Chronic Inflammation and Metabolic Syndrome through Mitochondria-Associated ER Membrane (MAM) Interaction and Pyruvate Dehydrogenase Kinase (PDK) Activity Regulation" in the research program titled "Personal Basic Research (Ministry of Science and ICT) (R&D)", by the Kyungpook National University Industry-Academic Cooperation Foundation, under management of the National Research Foundation of Korea, from 1 Mar. 2020 to 28 Feb. 2021.

This application claims priority to and the benefit of Korean Patent Application No. 10-2020-0120568 filed in the Korean Intellectual Property Office on 18 Sep. 2020, the disclosure of which is incorporated herein by reference.

The present disclosure relates to a composition containing a thiamine derivative for prevention, treatment, or alleviation of graft versus host disease and, more specifically, to a composition containing fursultiamine for prevention, treatment, or alleviation of graft versus host disease.

BACKGROUND ART

Graft versus host disease (GVHD) is a common complication of allogeneic bone marrow transplant (allo-BMT) in which functional immune cells in the transplanted marrow recognize the recipient as "foreign" and mount an immunologic attack. This is a pathological condition characterized by tissue damage of the recipient resulting from immune activation of donor T cells. Donor T cells typically show a response to foreign host cells in the gastrointestinal system, liver, and skin, and this occurs in 40-60% of patients receiving stem cell transplants.

Acute GVHD usually occurs within 100 days after transplantation, and chronic GVHD occurs 100 days after transplantation. Either acute or chronic form of GVHD occurs in approximately 40% of patients.

Acute GVHD is caused by the uncontrolled activation, migration, and proliferation of allogeneic donor T cells as well as the production of pro-inflammatory cytokines in GVHD target organs.

In contrast, the pathogenesis of chronic GVHD is associated with pathogenic T- and B-cell interactions and the generation of several immune cell types including T follicular helper (Tfh). Plasma cell differentiation and autoantibody production have also been demonstrated to contribute to disease pathology.

Broadly, GVHD occurs after stem cell transplantation has been performed, and is a rare disease considering that only a small number of patients receive stem cell transplantation. However, the incidence of GVHD among patients receiving stem cell transplantation is as high as 35-50%. The incidence of GVHD is estimated to be total about 5,500 cases each year.

The market for GVHD treatment is estimated to gradually increase to approximately 668 million USD by 2026 while recording a compound annual growth rate (CAGR) of 6.05% with an average annual sale of 4,000,000 USD during the period of 2019-2026. This rise in the market value is attribute to the growing awareness and interest in patients' health.

The global market for autoimmune disease medicines reached about 45 trillion Korean won in 2017 and is expected to reach about 61 trillion Korean won by 2025.

DETAILED DESCRIPTION OF THE INVENTION

Technical Problem

The present inventors verified that the administration of fursultiamine to a graft versus host disease (GVHD)-induced mouse model showed excellent effects in mitigating weight loss, reducing the degree of infiltration of inflammatory cells into the liver and colon, and inhibiting allogeneic CD4+ IFNg+ T cell generation.

An aspect of the present disclosure is to provide a pharmaceutical composition for prevention or treatment of graft versus host disease, the pharmaceutical composition containing at least one compound selected from the group consisting of a thiamine derivative represented by chemical formula 1 below and a pharmaceutically acceptable salt thereof:

[Formula 1]

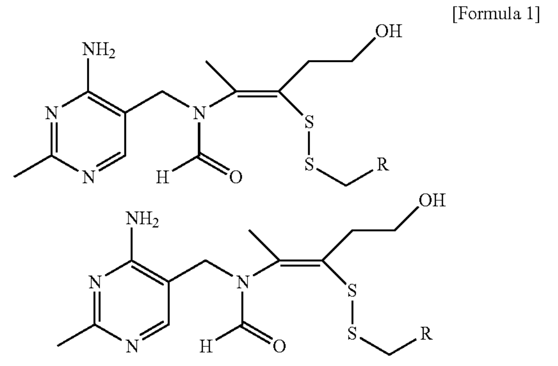

wherein R is any one selected from the group consisting of

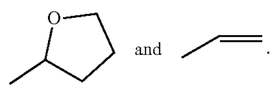

Another aspect of the present disclosure is to provide a food composition for alleviation of graft versus host disease, the pharmaceutical composition containing at least one compound selected from the group consisting of a thiamine derivative represented by chemical formula 1 below and a pharmaceutically acceptable salt thereof:

[Formula 1]

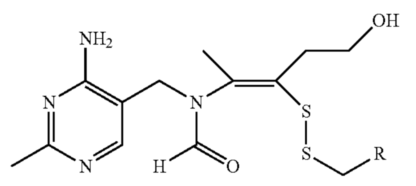

wherein R is any one selected from the group consisting of

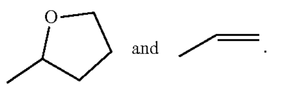

Still another aspect of the present disclosure is to provide use of a thiamine derivative for preventing, treating, or alleviating graft versus host disease.

Technical Solution

The present disclosure is directed to a composition containing a thiamine derivative for prevention, treatment, or alleviation of graft versus host disease (GVHD), and according to the present disclosure, fursultiamine can be used for preventing, treating, or alleviating graft versus host disease.

The present inventors verified that the administration of fursultiamine to a graft versus host disease animal model showed excellent effects in mitigating weight loss, reducing the degree of infiltration of inflammatory cells into the liver and colon, and inhibiting allogeneic CD4+IFNg+ cell generation.

Hereinafter, the present disclosure will be described in more detail.

In accordance with an aspect of the present disclosure, there is provided a pharmaceutical composition for prevention or treatment of graft versus host disease (GVHD), the pharmaceutical composition containing at least one compound selected from the group consisting of a thiamine derivative represented by chemical formula 1 below and a pharmaceutically acceptable salt thereof:

[Formula 1]

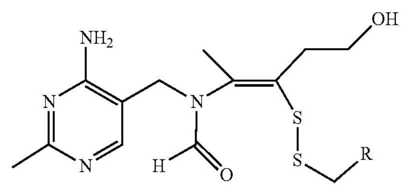

wherein R is any one selected from the group consisting of

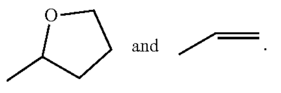

R may be

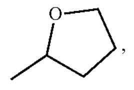

but is not limited thereto.

The thiamine derivative may be at least one selected from the group consisting of fursultiamine, allithiamine, and benfotiamine, and an example thereof may be fursultiamine, but are not limited thereto.

The graft versus host disease may occur in patients receiving the transplantation of stem cells or immune cells, for example, hematopoietic stem cells.

For example, the graft versus host disease occurs in cancer patients having undergone hematopoietic stem cell transplantation after receiving irradiation, but is not limited thereto.

The pharmaceutical composition of the present disclosure may be used as a pharmaceutical composition containing a pharmaceutically effective amount of a thiamine derivative and/or a pharmaceutically acceptable carrier.

As used herein, the term "pharmaceutically effective amount" refers to an amount that is sufficient to attain efficacy or activity of the aforementioned thiamine derivative.

The pharmaceutically acceptable carrier contained in the pharmaceutical composition of the present disclosure is commonly used in the formulation of medicines, and may include lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methyl hydroxybenzoate, propyl hydroxybenzoate, talc, magnesium stearate, and mineral oil, but is not limited thereto. The pharmaceutical composition of the present disclosure may further contain, in addition to the above ingredients, a lubricant, a wetting agent, a sweetening agent, a flavoring agent, an emulsifier, a suspending agent, a preservative, and the like.

The pharmaceutical composition according to the present disclosure may be administered to mammals including humans through various routes. The manner of administration may be any manner that is conventionally used, and the administration may be conducted through an oral, dermal, intravenous, intramuscular, or subcutaneous route, and for example, the administration may be conducted through an oral route.

The appropriate dose of the pharmaceutical composition of the present disclosure varies depending on factors, such as a formulating method, a manner of administration, patient's age, body weight, sex, and morbidity, food, a time of administration, a route of administration, an excretion rate, and response sensitivity. An ordinarily skilled practitioner can easily determine and prescribe the effective dose for the desired treatment or prevention. For example, the pharmaceutical composition of the present disclosure may be prescribed at 50 to 100 mg/kg, for example, 50 mg/kg daily. A dose of less than 50 mg/kg may show no therapeutic effects, and a dose of more than 100 mg/kg may cause weight loss to reduce therapeutic effects.

The pharmaceutical composition may be formulated using a pharmaceutically acceptable carrier and/or vehicle by a method that can be easily performed by a person having ordinary skills in the art to which the present disclosure pertains, so that the pharmaceutical composition can be prepared in a unit dose form or can be contained in a multi-dose container. The formulations may be in the form of a solution in an oily or aqueous medium, a suspension, an emulsion, an extract, a powder, granules, a tablet, a capsule, or a gel (e.g., a hydrogel), and may further contain a dispersant or a stabilizer.

In accordance with another aspect of the present disclosure, there is provided a food composition for alleviation of graft versus host disease, the pharmaceutical composition containing at least one compound selected from the group consisting of a thiamine derivative represented by chemical formula 1 below and a pharmaceutically acceptable salt thereof:

[Formula 1]

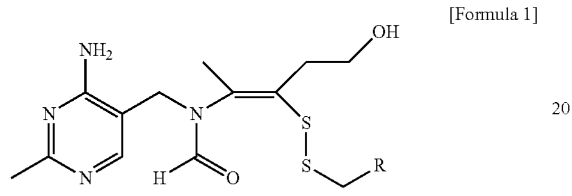

wherein R is any one selected from the group consisting of

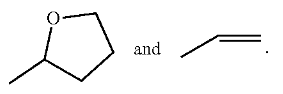

R may be

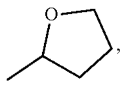

but is not limited thereto.

The thiamine derivative may be at least one selected from the group consisting of fursultiamine, allithiamine, and benfotiamine, and an example thereof may be fursultiamine, but are not limited thereto.

The graft versus host disease may occur in patients receiving the transplantation of stem cells or immune cells, for example, hematopoietic stem cells.

When the food composition of the present disclosure is used as a food additive, the food composition may be added as it is, or may be used along with other foods or food ingredients, and may be appropriately used by a conventional method.

The type of food is not particularly limited. Examples of the food to which the above-described materials may be added include meats, sausages, breads, chocolates, candies, snacks, confectioneries, pizzas, ramen, other noodles, gums, dairy products encompassing ice creams, various soups, beverages, teas, drinks, alcoholic beverages, vitamin complexes, and the like, and include all foods in a typical sense.

The beverage may contain, as additive ingredients, various kinds of flavoring agents or natural carbohydrates. The aforementioned natural carbohydrates may include monosaccharides such as glucose and fructose, disaccharides such as maltose and sucrose, natural sweeteners such as dextrin and cyclodextrin, and synthetic sweeteners such as saccharin and aspartame. The proportions of the natural carbohydrates may be appropriately determined by the selection of a person skilled in the art.

In addition to the aforementioned ingredients, the food composition of the present disclosure may contain various types of nutrient supplements, vitamins, electrolytes, flavoring agents, colorants, pectic acid and salts thereof, alginic acid and salts thereof, organic acids, protective colloid thickeners, pH adjusters, stabilizers, preservatives, glycerin, alcohols, carbonizing agents used in carbonated beverages, and the like. Furthermore, the food composition of the present disclosure may contain fruit flesh for manufacturing natural fruit juices, fruit juice drinks, and vegetable drinks. These ingredients may be used either alone or in combination. The proportions of these ingredients may also be appropriately selected by a person skilled in the art.

Advantageous Effects

The present disclosure is directed to a composition containing a thiamine derivative for prevention, treatment, or alleviation of graft versus host disease (GVHD), wherein fursultiamine, which is an active ingredient of the pharmaceutical composition, can mitigate weight loss, reduce the degree of infiltration of inflammatory cells into the liver and colon, and effectively inhibit allogeneic CD4+IFNg+ T cell generation, and thus can be effectively used in the prevention, treatment, or alleviation of graft versus host disease.

BEST MODE FOR CARRYING OUT THE INVENTION

The present disclosure is directed to a pharmaceutical composition for prevention or treatment of graft versus host disease (GVHD), the pharmaceutical composition containing at least one compound selected from the group consisting of a thiamine derivative represented by chemical formula 1 below and a pharmaceutically acceptable salt thereof:

[Formula 1]

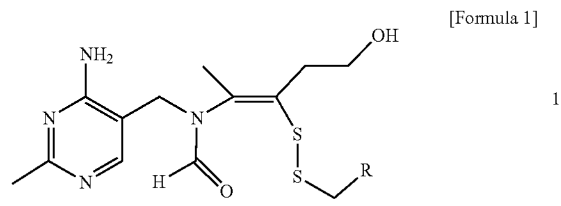

wherein R is any one selected from the group consisting of

[Formula 1]

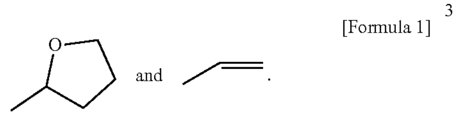

and

.

MODE FOR CARRYING OUT THE INVENTION

Hereinafter, the present disclosure will be described in more detail by the following examples. However, these exemplary embodiments are used only for illustration, and the scope of the present disclosure is not limited by these exemplary embodiments.

Throughout the present specification, the "%" used to express the concentration of a specific material, unless otherwise particularly stated, refers to (wt/wt) % for solid/solid, (wt/vol) % for solid/liquid, and (vol/vol) % for liquid/liquid.

Example 1: Effect of Thiamine Derivatives on Allo-Reactive CD4+IFNg+ T Cell Generation A high amount of CD4+IFNg+ T cell generated can be inferred to allow the proliferation of T cells against allogenic antigens, thereby attacking the body organs of a patient. Therefore, a graft versus host disease (GVHD) in vitro validation model was subjected to a mixed lymphocyte reaction to compare the degree of allo-reactive CD4+IFNg+ T cell generation among thiamine derivatives by flow cytometry.

Specifically, BALB/c mice were sacrificed by cervical dislocation, and then the spleens were extracted, followed by erythrocyte lysis using ACK lysing buffer. Thereafter, the isolated spleen cells were irradiated at 2500 cGy.

A syngeneic control group was prepared by mixing 8×105 BALB/c mouse-derived irradiated splenocytes and 8×105 BALB/c-derived irradiated CD4+ T cells, and a positive control group was prepared by mixing 8×105 BALB/c mouse-derived irradiated splenocytes and 8×105 C57BL6/J mouse-derived CD4+ T cells. The positive group was treated with 10, 50, and 100 uM benfotiamine, 1, 5, and 10 uM allithiamine, and 10, 50, and 100 uM fursultiamine to prepare experimental groups.

Thereafter, the cells were cultured in RPMI1640 (10% FBS, 1% penicillin streptomycin) at 37° C. for 5 days, and the cells were separated, followed by flow cytometry, to investigate the degree of CD4+IFNg+ T cell generation.

TABLE 1

| | Syngeneic | Positive | Benfotiamine (μM) | | | Allithiamine (μM) | | | Fursultiamine (μM) | | |
|---|---|---|---|---|---|---|---|---|---|---|---|
| | control | control | 10 | 50 | 100 | 1 | 5 | 10 | 10 | 50 | 100 |
| Amount of generation (%) | 15.3 | 37.4 | 36.8 | 43.9 | 40.1 | 35.2 | 25.7 | 23.9 | 34.9 | 13.6 | 12.5 |

Figure 1:
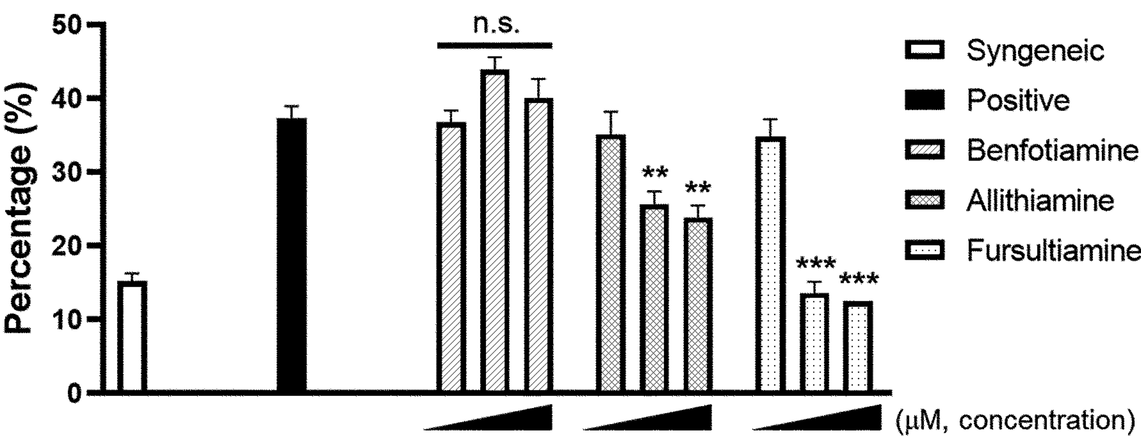
FIG. 1 is a graph illustrating an CD4+IFNg+ T cell generation inhibiting effect of a thiamine derivative in the mixed lymphocyte reaction induction experiment using mouse cells according to an example of the present disclosure.

As can be seen from Table 1 and FIG. 1, the treatment with benfotiamine showed no significant difference in the degree of generation of CD4+IFNg+ T cells, compared with the positive control, regardless of the concentration of benfotiamine. However, allithiamine at 5 uM or more and fursultiamine at 50 uM or more showed a significant reduction compared with the positive control, in a concentration dependent manner.

Example 2: Treatment Effect of Fursultiamine in GVHD Disease Model

Figure 2A:
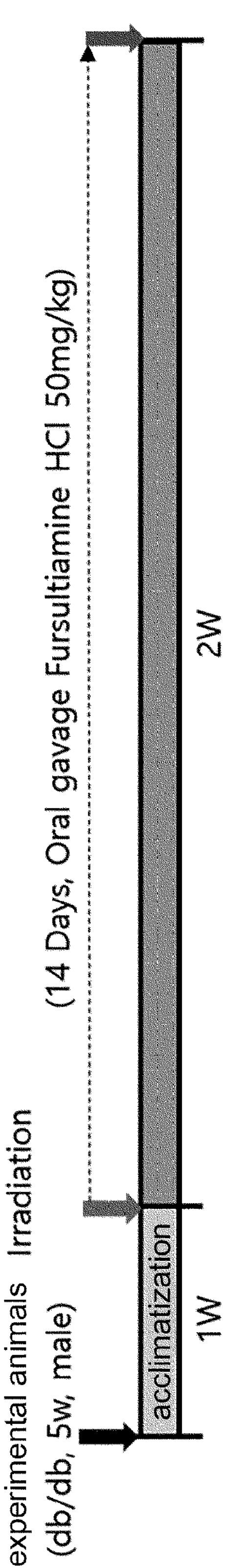
FIG. 2A is a schematic diagram of the construction of graft versus host disease (GVHD) model mice and the administration procedure of fursultiamine according to an example of the present disclosure.

Referring to FIG. 2A, 5-week-old BALB/c male mice were acclimatized for 1 week, irradiated with 800 cGy radiation throughout the body, and then injected with 5×106 C57BL/6J-derived bone marrow cells and 1×107 splenocytes derived therefrom via IV injection, thereby constructing a GVHD in vivo model (positive control group, Positive). The syngeneic control group (Syngeneic) was constructed in the same manner as above while BALB/c-derived bone marrow cells were selected as the bone marrow cells to be injected.

The fursultiamine administration group (Fur50) was constructed by daily oral gavage of fursultiamine HCl at 50 mg/kg to the GVHD in vivo model.

The treatment effect of fursultiamine was investigated on the constructed experimental groups by measuring the change in weight every 3 days.

Figure 2B:
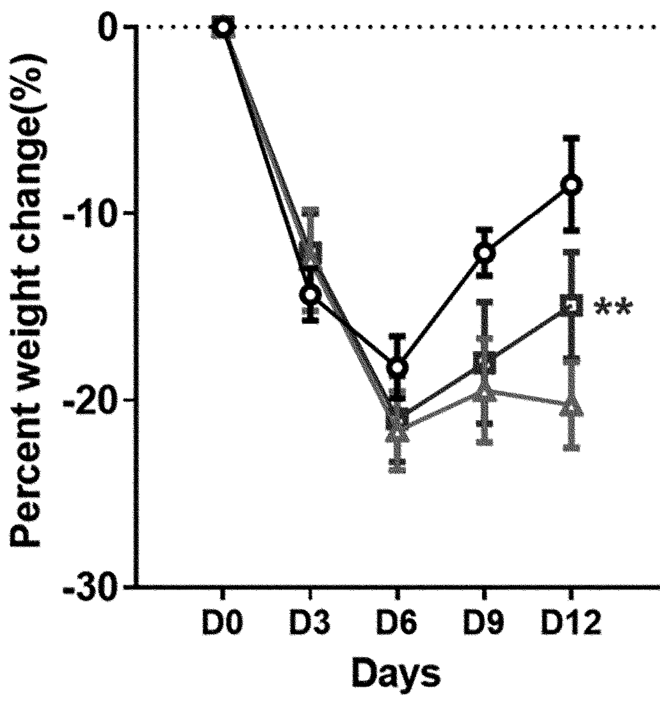
FIG. 2B is a graph illustrating weight changes of the graft versus host disease model mice according to an example of the present disclosure.

As can be seen from FIG. 2B, the fursultiamine administration group showed a significant recovery compared with the GVHD in vivo model on Day 12 of oral administration.

On Day 14, the comparison between the amounts of generation of CD4+ T cells and CD4+IFNg+ T cells, which are major factors causing GVHD, was performed in the spleens isolated from the mice.

TABLE 2

| | Syngeneic control | Positive control | Fursultiamine administration |
|---|---|---|---|
| Amount of generation of CD4+ T cells (%) | 6.9 | 21.1 | 13.4 |
| Amount of generation of CD4+IFNg+ T cells (%) | 3.2 | 18.3 | 12.6 |

Figure 2C:
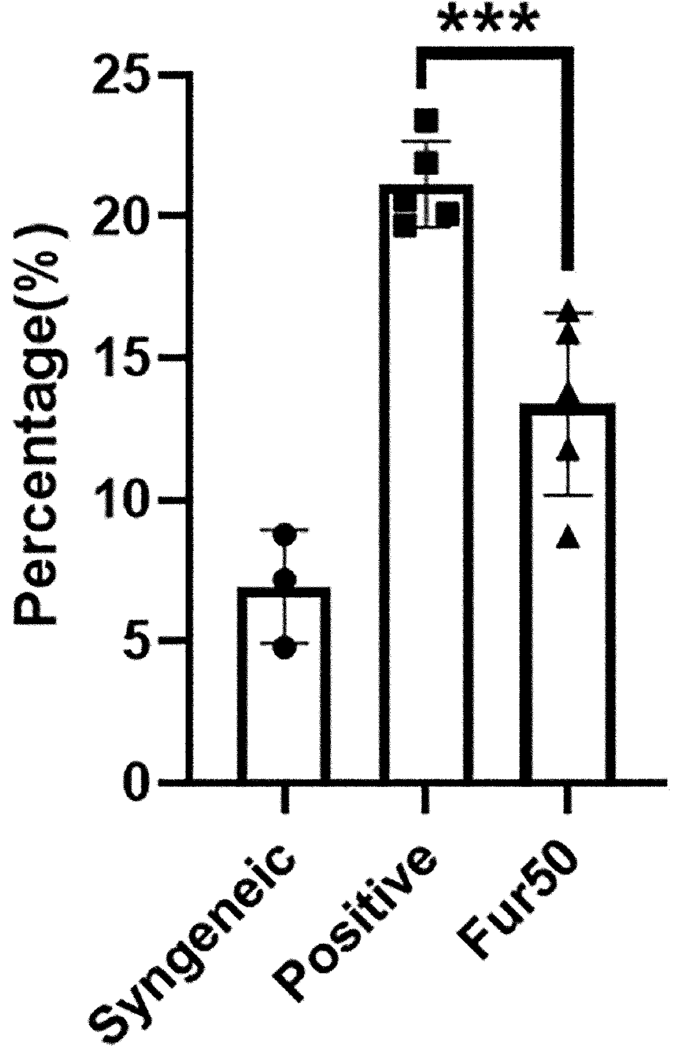
FIG. 2C is a graph illustrating the change in amount of generation of CD4+ T cells in the spleens isolated from the graft versus host disease model mice according to an example of the present disclosure.
Figure 2D:
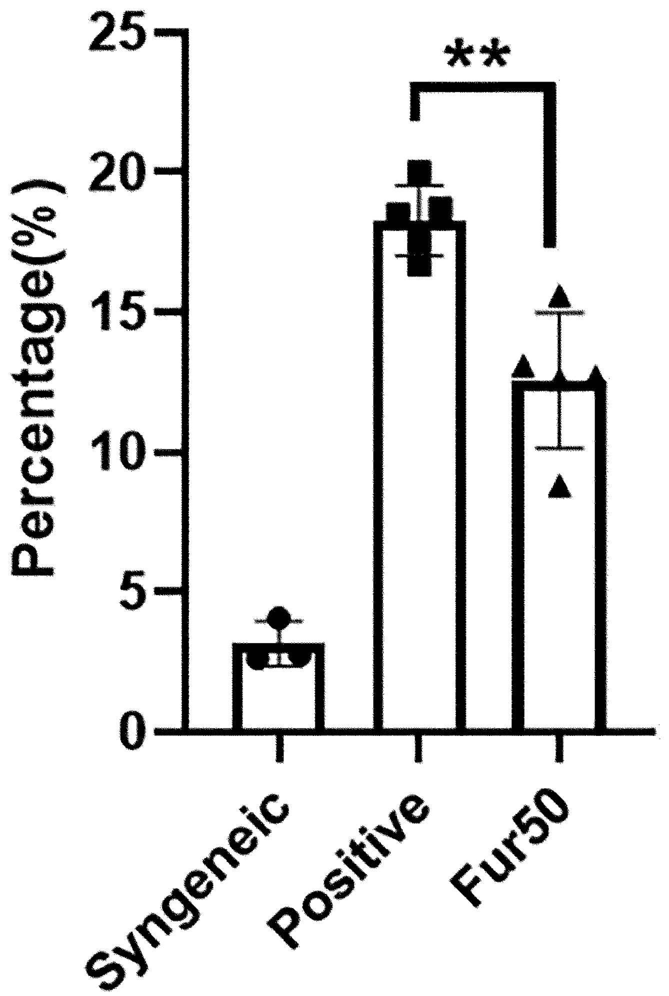
FIG. 2D is a graph illustrating the change in amount of generation of CD4+IFNg+ T cells in the spleens isolated from the graft versus host disease model mice according to an example of the present disclosure.

As can be seen from Table 2 and FIGS. 2C and 2D, the amounts of generation of allogenic CD4+ T cells and CD4+IFNg+ T cells were reduced by fursultiamine administration. On Day 14 of inducing the GVHD in vivo model, liver and large intestine tissues were extracted from the mice, fixed in 4% paraformaldehyde for 48 hours, and then embedded in paraffin. The resultant tissues were sliced into 5 μm sections and then subjected to hematoxylin and eosin (H&E) staining. (bar=100 um)

Figure 2E:
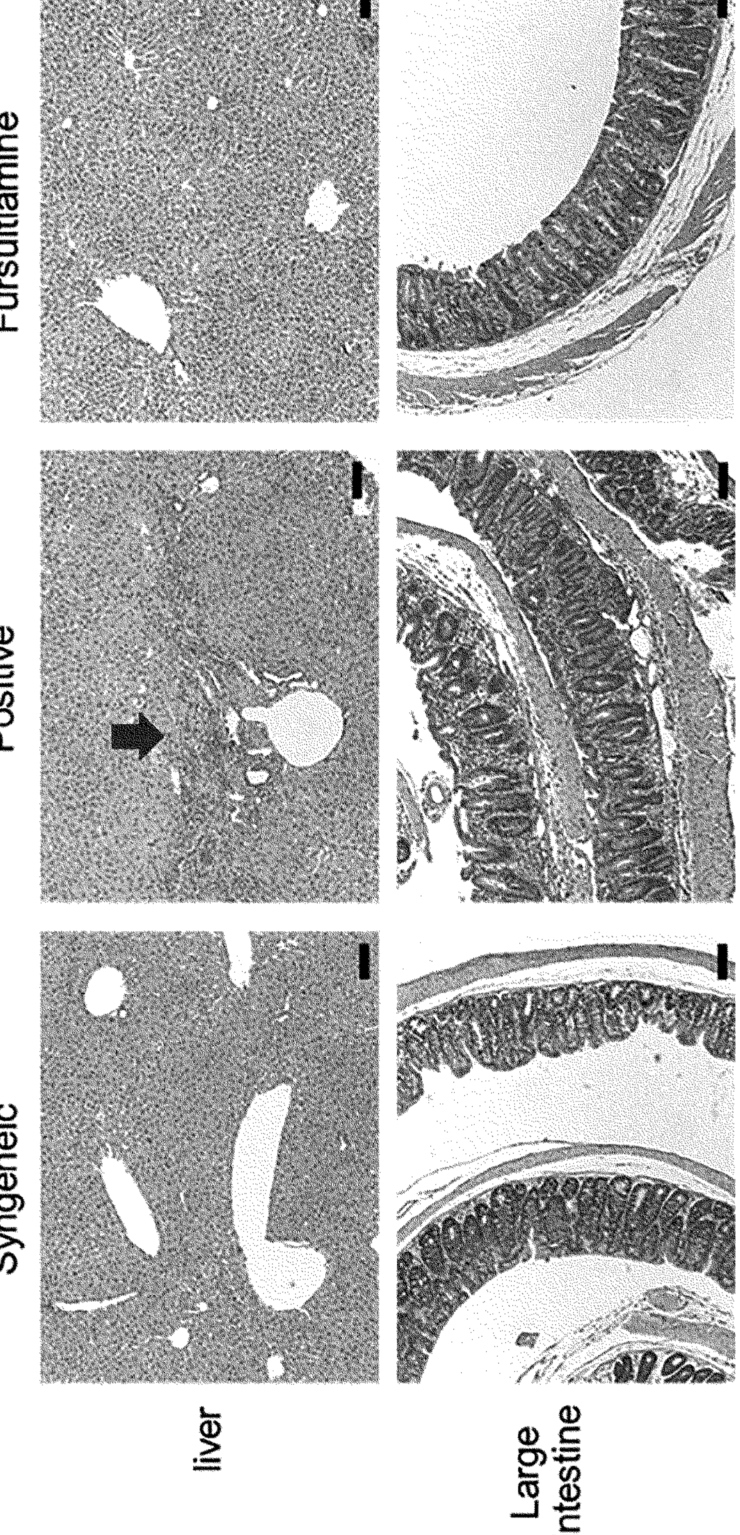
FIG. 2E shows hematoxylin and eosin (H&E) staining images of liver and large intestine tissues isolated from the graft versus host disease model mice according to an example of the present disclosure.

As can be seen from FIG. 2E, the infiltration of immune cells (indicated by the red arrow) was observed in the liver tissue of the positive control group, but the infiltration of immune cells was reduced in the fursultiamine administration group.

INDUSTRIAL APPLICABILITY

The present disclosure relates to a composition containing a thiamine derivative for prevention, treatment, or alleviation of graft versus host disease and, more specifically, to a composition containing fursultiamine for prevention, treatment, or alleviation of graft versus host disease.

What is claimed is:

1. A method for treating graft versus host disease (GVHD), comprising step of:

administering a pharmaceutical composition comprising at least one compound selected from the group consisting of a thiamine derivative represented by chemical formula 1 below and a pharmaceutically acceptable salt thereof to a subject

[Formula 1]

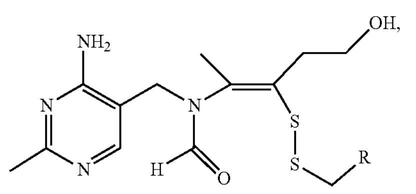

wherein R is any one selected from the group consisting of

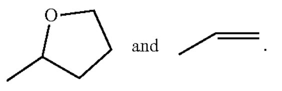

2. The method of claim 1, wherein R is

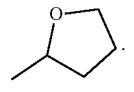

3. The method of claim 1, wherein the thiamine derivative is at least one selected from the group consisting of fursultiamine and allithiamine.

4. The method of claim 1, wherein the graft versus host disease occurs in cancer patients undergoing hematopoietic stem cell transplantation after receiving irradiation.

5. A method for alleviating graft versus host disease (GVHD), comprising step of:

administering a food composition comprising at least one compound selected from the group consisting of a thiamine derivative represented by chemical formula 1 below and a pharmaceutically acceptable salt thereof to a subject

[Formula 1]

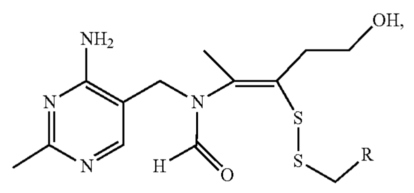

wherein R is any one selected from the group consisting of

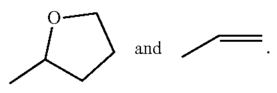

6. The method of claim 5, wherein R is

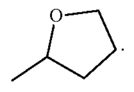

7. The method of claim 5, wherein the thiamine derivative is at least one selected from the group consisting of fursultiamine and allithiamine.

8. The method of claim 5, wherein the graft versus host disease occurs in cancer patients undergoing hematopoietic stem cell transplantation after receiving irradiation.

* * * * *